United States Patent [19]

Rosenblatt

[11] 4,431,742

[45] Feb. 14, 1984

[54] RADIORECEPTOR ASSAY FOR BENZODIAZEPINES IN SALIVA

[75] Inventor: Jack E. Rosenblatt, Bethesda, Md.

[73] Assignee: The United States of America as represented by the Department of Health and Human Services, Washington, D.C.

[21] Appl. No.: 249,229

[22] Filed: Mar. 30, 1981

Related U.S. Application Data

[63] Continuation of Ser. No. 14,552, Feb. 23, 1979, abandoned.

[51] Int. Cl.$^3$ .................. G01N 33/60; A61K 43/00
[52] U.S. Cl. .................. 436/504; 436/804; 436/815
[58] Field of Search .................. 424/1, 12; 23/230 B; 436/504, 804, 815

[56] References Cited

U.S. PATENT DOCUMENTS

| | | | |
|---|---|---|---|
| 4,058,511 | 11/1977 | Singh | 23/230 B |
| 4,083,948 | 4/1978 | Davis et al. | 424/1 |
| 4,119,709 | 10/1978 | Holub | 424/1 |
| 4,191,738 | 3/1980 | Dixon | 424/1 |
| 4,197,288 | 4/1980 | Snyder | 424/1 |
| 4,239,744 | 12/1980 | Paul et al. | 424/1 |

OTHER PUBLICATIONS

*The Benzodiazepines,* Ed. Garatini, Raven Press, N.Y., 1973, pp. 75-97.
Braestrup et al., Proc. Natl. Acad. Sci., vol. 74, Sep., 1977, pp 3805-3809.
Squires et al., Nature, vol. 266 Apr. 21, 1977, pp. 732-734.

*Primary Examiner*—Christine M. Nucker
*Attorney, Agent, or Firm*—John S. Roberts, Jr.

[57] ABSTRACT

A radioreceptor assay for benzodiazepines in saliva which comprises measuring the diminution of attachment of a known quantity of radio labeled benzodiazepine to a receptor carrier in the presence of an unknown quantity of unlabeled benzodiazepine in a known amount of human saliva. Benzodiazepines are selected from the following oft-utilized drugs which are also representative types of benzodiazepine; namely, diazepam (Valium), chlordiazepoxide (Librium), nitrazepam (Benzalin), oxazepam (Serax), flurazepam (Dalmane), and clorazepate.

Competitive receptors suitable for the present benzodiazepine radioreceptor assay are from fresh rat frontal cortex. Utilizable receptors are whole brain cortex, human cortex, and striatum.

6 Claims, 1 Drawing Figure

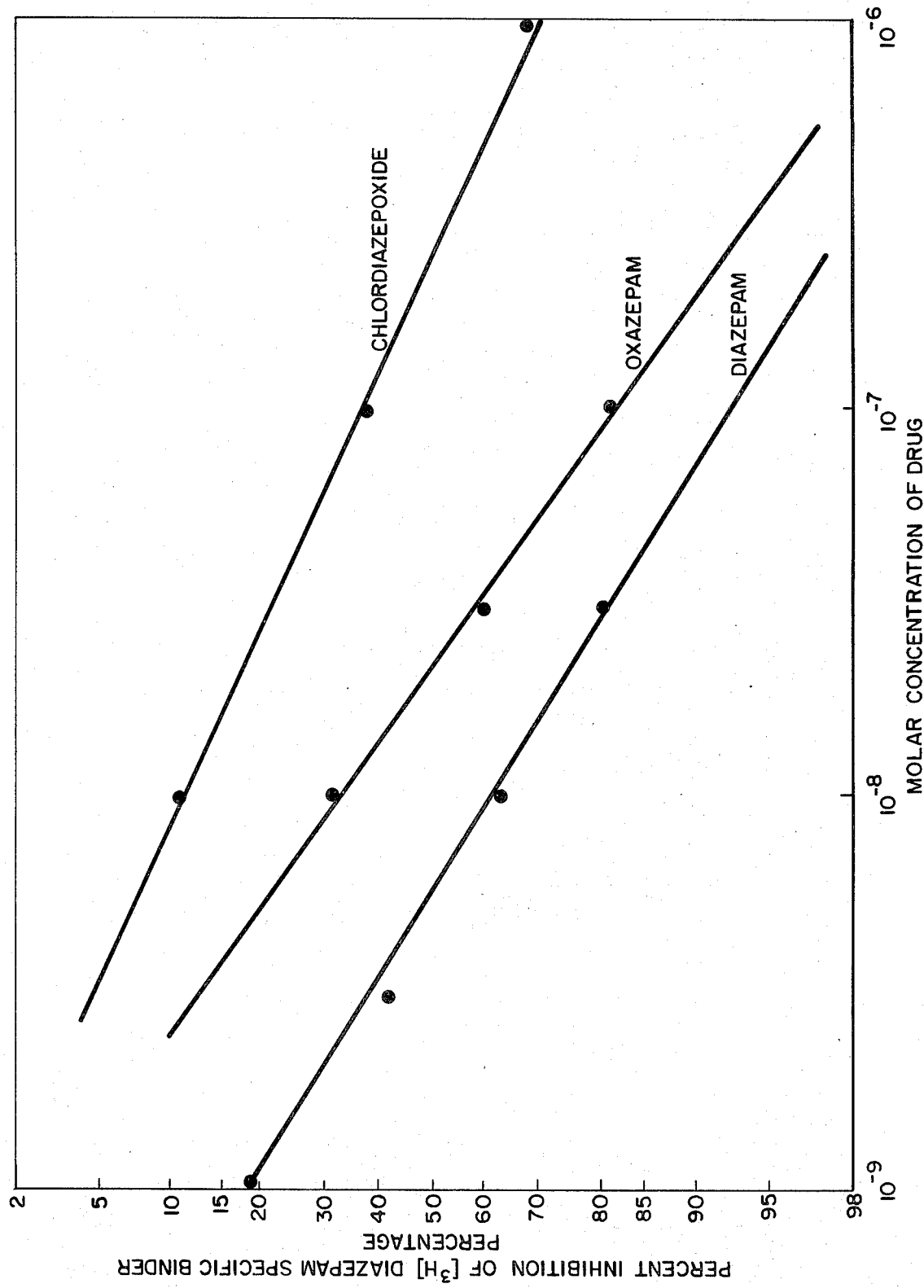

RADIORECEPTOR ASSAY FOR BENZODIAZEPINES IN SALIVA

This is a continuation of application Ser. No. 014,552, filed Feb. 23, 1979, now abandoned.

This invention relates to a radioreceptor assay for benzodiazepines in saliva which comprises measuring the diminution of attachment of a known quantity of radio labeled benzodiazepine to a receptor carrier in the presence of an unknown quantity of unlabeled benzodiazepine in a known amount of human saliva. Benzodiazepines are selected from the following formulae of oft-utilized drugs:

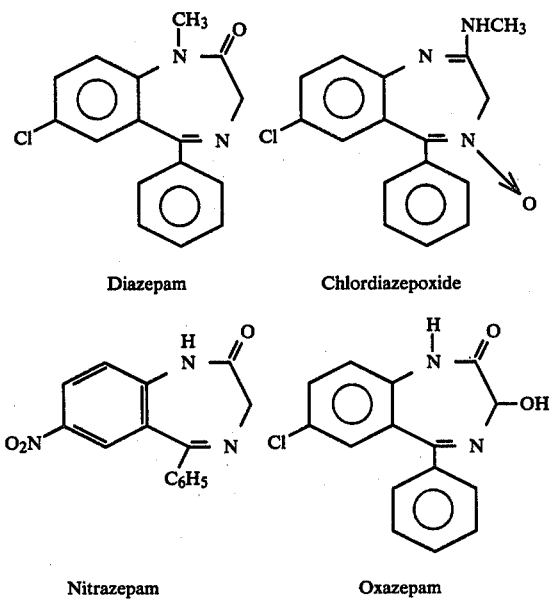

Diazepam    Chlordiazepoxide

Nitrazepam    Oxazepam

The above structural formulae are illustrative of a larger group of active compounds, such as diazepam (Valium), chlordiazepoxide (Librium), nitrazepam (Benzalin), oxazepam (Serax), flurazepam (Dalmane), and clorazepate. Competitive receptors suitable for the present benzodiazepine radioreceptor assay are from fresh rat frontal cortex. Utilizable receptors are whole brain cortex, human cortex, and striatum. The basic utility of active members of the benzodiazepines is as a clinical anxiety reliever or hypnotic.

The benzodiazepines are the most commonly used prescription drugs in this country. They are commonly used to treat anxiety and insomnia and are increasingly being used to treat alcohol withdrawal symptoms and epileptic seizures. Routine monitoring of benzodiazepine concentrations would be desirable for many reasons. Patient dose requirements vary widely due to the wide range of blood levels reported following the same dose. Because benzodiazepine side effects, such as lethality when mixed with alcohol, and the risk of physiological and psychological dependence are apparently does related, patients should be maintained on the lowest effective therapeutic dose. Although threshold levels must be attained for therapeutic efficacy, excessive levels may cause clinical worsening.

PRIOR ART STATEMENT

U.S. Pat. No. 4,083,948 Davis et al. (Hoffmann-LaRoche) is a radioimmunoassay for benzodiazepines using preferably $^{125}$I-labeled 4'-hydroxy derivatives of these compounds as tracers.

U.S. Pat. No. 4,119,709 Holub is a diagnostic test based on competitive binding where there is a difference for the radioactive labeled form of the substance between liquid and solid phases.

M. A. Schwartz, "Pathways of Metabolism of the Benzodiazepines," The Benzodiazepines, ed. by S. Garattini et al., New York, Raven Press, 1973, pp. 75-97.

C. Brasestrup et al., "Specific Benzodiazepine Receptors in Rat Brain Characterized by High Affinity [$^3$H] Diazepam Binding," *Proc. Natl. Acad. Sci.*, 74(9):3805-3809, 1977.

R. F. Squires, "Benzodiazepine Receptors in Rat Brain," *Nature*, 266:732-734, 1977.

In the literature the principal method for measuring benzodiazepines, gas liquid chromatography, has not attained routine clinical use because of technical complexities. Also, development of a specific assay is required for each drug and its metabolites. In this invention there is described an assay for benzodiazepines in saliva based on competition for diazepam receptor binding. The assay is sensitive and simple enough for routine clinical use. Measurement of benzodiazepines in saliva offers advantages over plasma level determinations; saliva is easier to collect, particularly from anxious patients, and faster to assay. Also, saliva more directly reflects an intracellular environment and thus may correspond more closely to clinical efficacy than plasma level.

The following description represents the best mode for carrying out the present invention as well as one or more specific examples or embodiments of the working thereof.

In this assay, saliva is used without any extraction or precipitation. The saliva is first centrifuged (10,000 g for 20 mins) to separate it into mucous sediment and serous supernatant. The serous supernatant is diluted by a factor of two with 50 mM Tris buffer pH 7.7 at 25° C. [tris(hydroxymethyl)aminomethane] and added directly to the assay. The absence of interference by saliva itself is apparent from experiments in which 100λ of diluted saliva in a total assay volume of 0.5 ml reduced $^3$H-diazepam binding by only 1.60±0.08%. Increasing volumes of saliva reduced binding linearly with about 45% inhibition occurring with 100λ of saliva. Saliva reduces specific and non-specific binding to the same extent, suggesting that saliva proteins bind $^3$H-diazepam, making less available for interaction with brain membranes. The inhibition of binding by the saliva of several laboratory personnel was uniform, as was inhibition of binding by the same subjects' saliva collected on different days. Variability of inhibition of specific binding for repeated determinations of the same sample was less than 5%.

In summary, the simplicity of the benzodiazepine receptor assay for saliva, as well as the ease with which saliva samples (0.2 ml each) can be collected and stored, make this assay suitable for routine clinical use in large patient populations. Saliva can be collected at home and refrigerated for later assay. The assay is selective; chlorpromazine ($10^{-5}$M), haloperidol ($10^{-5}$M), pimozide ($10^{-5}$M), fluphenazine ($10^{-5}$M), desmethylimipramine ($10^{-5}$M), pargyline ($10^{-5}$M), dl-propranolol ($10^{-5}$M), and levallorphan ($10^{-5}$M) incubated with saliva failed to inhibit $^3$H-diazepam binding more than saliva itself, suggesting that this assay can be used in patients who are being treated with a variety of other drugs besides benzodiazepines. For patients receiving more than one benzodiazepine, the absolute concentration of each cannot be determined separately. In such cases, inhibition of $^3$H-diazepam binding would be converted to a diazepam equivalent which would produce the same degree of inhibition.

The radioreceptor assay for benzodiazepine in saliva is simpler to perform than would be a radioreceptor assay for benzodiazepines in plasma (red blood cells). There is a high degree of inhibition of $^3$H-diazepam specific and non-specific binding by both plasma and red blood cell lysates. This necessitates extra steps for further purification of plasma by deproteination and centrifugation. In the radioreceptor assay for benzodiazepines in saliva, this is not necessary. Dilute serous saliva is added directly to the assay without further extraction or purification. Large amounts of cortex can be obtained from rats and stored frozen. $^3$H-diazepam is commerically available. It is believed that 100 samples can be assayed in a day.

EXAMPLE 1

Competition by Inhibition Caused by Drug-Free Saliva

Benzodiazepines in saliva reduce the specific binding of $^3$H-diazepam more than the small degree of inhibition caused by drug-free saliva and the amount of inhibition of specific binding is proportional to the amount of benzodiazepine in saliva. The amount of benzodiazepine in a saliva sample can easily be determined using a standard curve of inhibition of $^3$H-ligand binding by known amounts of the drug.

This method requires that benzodiazepines present in saliva will not inhibit non-specific (blank) binding of $^3$H-ligand. In 14 saliva samples from patients on benzodiazepines, blank $^3$H-diazepam binding was 231±5 CPM, while non-specific binding in the presence of 12 control saliva samples was 205±7 CPM. Thus, specific binding in the presence of patient saliva can be determined by subtracting non-specific binding values obtained with control saliva from total binding with patient saliva. The percentage inhibition of specific $^3$H-diazepam binding (in the presence of control saliva) by the patient saliva (containing drug) was then calculated and compared to a standard displacement curve for determining actual benzodiazepine content.

Similar reductions in specific and non-specific binding of $^3$H-diazepam by saliva indicated that saliva components bind benzodiazepines making less available for membrane binding. In this assay, benzodiazepine bound to saliva components dissociates during the incubation so that total benzodiazepine levels were measured. To confirm this, 100 nM diazepam was pre-incubated for 10 mins at 37° C. with control saliva to allow binding to saliva proteins to occur. The saliva with diazepam was then added to a standard binding assay. The time course and extent of reduction of binding was the same for diazepam pre-incubated with saliva and diazepam dissolved in buffer. The maximum percentage lowering of binding was equivalent to that produced by 100 nM diazepam added directly to the assay with no saliva present.

For the benzodiazepine radioreceptor assay, fresh rat frontal cortex was homogenized (Brinkman polytron, setting 6 for 30 secs) in 50 volumes (w/v) 50 mM Tris buffer, pH 7.4 at 25° C. The homogenate was centrifuged twice at 50,000 g for 10 mins, with re-homogenization of the intermediate pellet in fresh buffer. The final pellet (which may be stored frozen) was resuspended in 15 volumes of freshly prepared 50 mM Tris buffer, pH 7.4 at 25° C. $^3$H-diazepam (80 Ci mmol$^{-1}$, New England Nuclear) was diluted to 5 nM in fresh buffer. Polypropylene 12×75 mm incubation tubes received, in order, 100λ diluted saliva (on benzodiazepine therapy or drug free), 50λ $^3$H-ligand, 50λ drug for standard curve or nitrazepam for blanks (final concentration 1 micromolar) or the drug solvent buffer, and tissue suspension to 0.5 ml total volume. Final concentration of $^3$H-diazepam was 0.50 nM. The tubes were incubated at 0° C. for 45 mins and rapidly filtered under vacuum through Whatman GF/B filters with two 5 ml rinses of ice cold 50 mM Tris buffer pH 7.4 at 25° C. $^3$H-diazepam trapped on the filters was counted by liquid scintillation spectrometry after remaining overnight in scintillation vials containing Aquasol (New England Nuclear). A standard displacement curve for the drug under study was determined in the presence of equal volumes of control saliva with final concentrations of drug about one-third, three times, and the same as its IC50 value for inhibiting $^3$H-diazepam binding under the conditions described. A log-probit plot was used to convert the displacement curve to a straight line, allowing percentage inhibition of $^3$H-diazepam to be converted to molar drug concentration (FIG. 1).

To examine recovery, four different benzodiazepines were pre-incubated with saliva for 10 mins at 37° C. to provide time for binding to saliva proteins and subsequently assayed for benzodiazepine levels. Diazepam (100 nM), chlordiazepoxide (1000 nM), nitrazepam (100 nM), and oxazepam (100 nM) were all fully recovered in the benzodiazepine radioreceptor assay with respective values of 97 nM (n=4), 1000 nM (n=4), 100 nM (n=4), and 100 nM (n=4).

EXAMPLE 2

This example compares the present radioreceptor assay and its saliva levels with another procedure which is gas liquid chromatography with electron capture.

Saliva benzodiazepine levels were measured in patients treated with oxazepam; saliva oxazepam levels were determined on the same samples by gas liquid chromatography with electron capture and by saliva radioreceptor assay. Table 1 indicates a good agreement between the different methods. Using 100λ of two-fold diluted saliva, the lower limit of sensitivity (7% inhibition of specific binding) is 0.14 ng/ml, 1.50 ng/ml, 0.28 ng/ml, and 2.87 ng/ml for diazepam, chlordiazepoxide, nitrazepam and oxazepam, respectively.

TABLE 1

Results of Split Sample Determinations Using the Radioreceptor Assay and Gas-Liquid Chromatography With Electron Capture

| Sample | Radioreceptor Assay | Gas-Liquid Chromatography with Electron Capture |
|---|---|---|
| 1 | 17.2 | 16.8 |
| 2 | 17.2 | 17.9 |
| 3 | 20.1 | 19.6 |
| 4 | 16.7 | 20.3 |
| 5 | 15.5 | 16.7 |
| 6 | 18.9 | 18.6 |
| 7 | 28.7 | 28.7 |
| 8 | 28.7 | 29.9 |

(Intraclass correlation = 0.95; p<.0001)

I claim:

1. In a radioreceptor assay for benzodiazepine in saliva which comprises measuring the diminution of attachment of a known quantity of radiolabeled benzodiazepine to a receptor carrier in the presence of an unknown quantity of unlabeled benzodiazepine in a known amount of human saliva, the improvement wherein
   (1) the saliva is centrifuged to separate mucous sediment and serous supernatant;
   (2) the serous supernatant is diluted and incubated with radiolabeled benzodiazepine and receptor carrier at 0° C. for about 45 minutes, wherein the receptor carrier is fresh brain cortex or striatum homogenized and formed into a pellet.

2. The method according to claim 1 wherein the unlabeled benzodiazepine is diazepam.

3. The method according to claim 1 wherein the unlabeled benzodiazepine is chlordiazepoxide.

4. The method according to claim 1 wherein the unlabeled benzodiazepine is nitrazepam.

5. The method according to claim 1 wherein the unlabeled benzodiazepine is oxazepam.

6. The method according to claim 1 wherein the radio labeling is by $^3H$.